United States Patent [19]

Tsuchiya et al.

[11] 4,150,966

[45] Apr. 24, 1979

[54] METHOD FOR CULTIVATION OF TOBACCO PLANTS

[75] Inventors: Hideshi Tsuchiya, Tokyo; Tetsuo Takamatsu, Utsunomiya; Masakazu Furushima, Niigata; Shiro Hojo, Marugame, all of Japan

[73] Assignees: Mitsubishi Gas Chemical Company, Inc.; Japan Hydrazine Co., Inc., both of Tokyo, Japan

[21] Appl. No.: 777,543

[22] Filed: Mar. 14, 1977

Related U.S. Application Data

[63] Continuation of Ser. No. 600,479, Jul. 30, 1975, abandoned.

[30] Foreign Application Priority Data

Jul. 31, 1974 [JP] Japan .................. 49-87071

[51] Int. Cl.² ............................................. A01N 5/00
[52] U.S. Cl. ........................................... 71/78; 71/92
[58] Field of Search .................. 71/78, 92; 260/250 A

[56] References Cited

U.S. PATENT DOCUMENTS

| | | | |
|---|---|---|---|
| 2,614,916 | 10/1952 | Hoffmann et al. | 71/92 |
| 2,805,926 | 9/1957 | Schoene et al. | 71/92 |
| 3,395,009 | 7/1968 | Oettel et al. | 71/76 |

OTHER PUBLICATIONS

Tsuchiya et al., "Maleic Acid Hydrazide, etc.," (1974) CA 82, No. 39576k. (1975).
Germane et al., "Initial Toxicological Appraisal, etc.," (1973) CA 80, No. 23311t. (1974).
Schoene et al. II, "Maleic Hydrazide, a Unique, etc.," (1949) CA 43, p. 6776 (1949).

*Primary Examiner*—Glennon H. Hollrah
*Attorney, Agent, or Firm*—Haseltine, Lake & Waters

[57] ABSTRACT

Tobacco yield is increased by spraying the plants after topping with an effective amount of an aqueous solution of the choline salt of maleic hydrazide.

2 Claims, 2 Drawing Figures

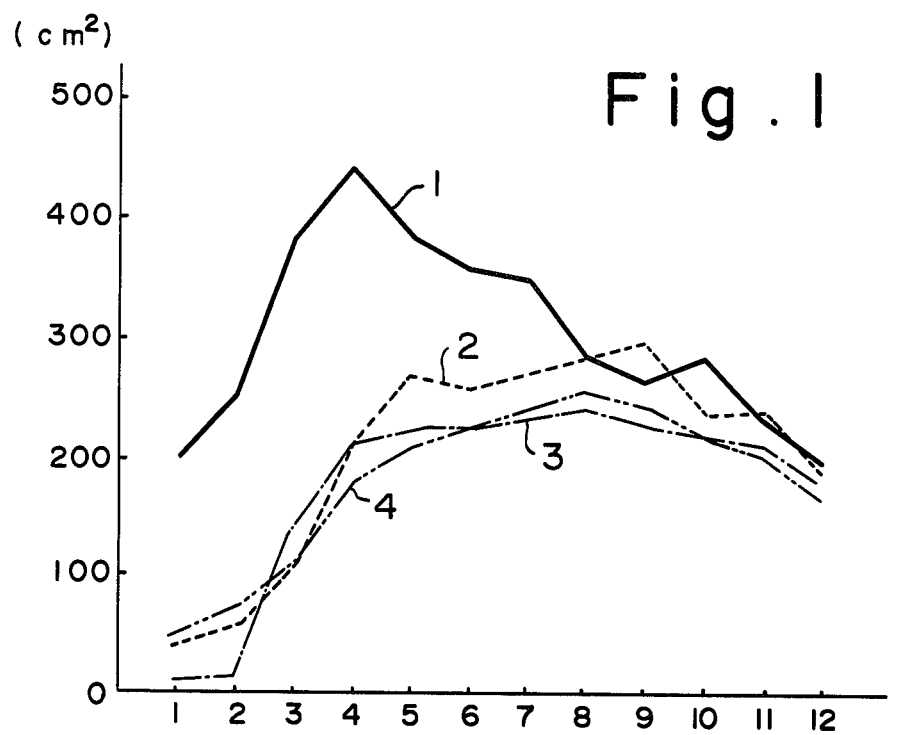
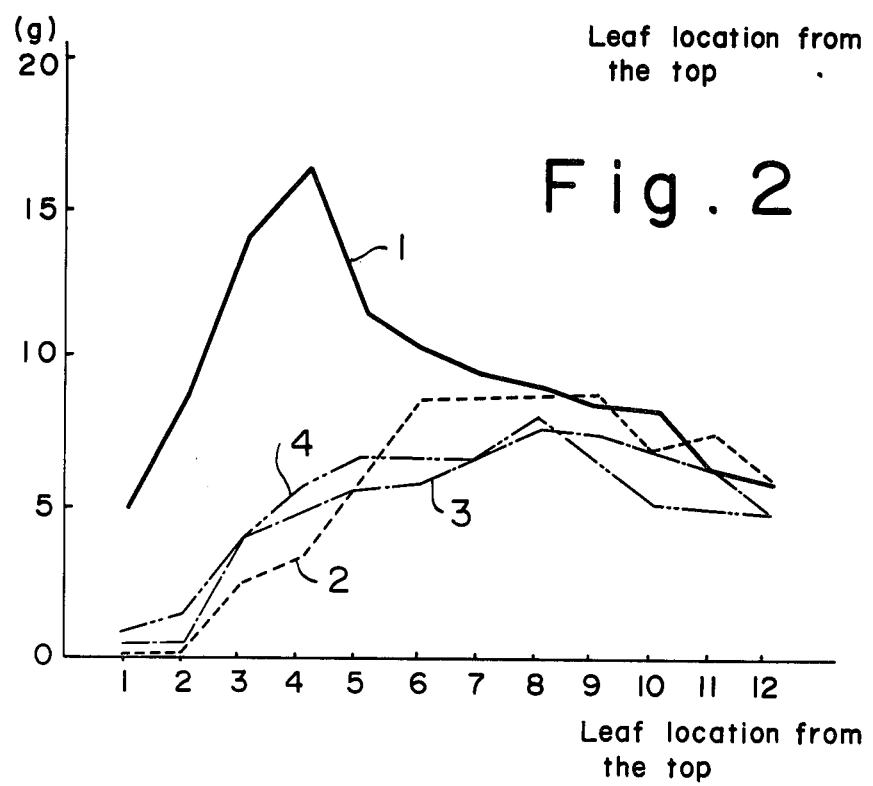

METHOD FOR CULTIVATION OF TOBACCO PLANTS

This is a continuation of application Ser. No. 600,479 filed July 30, 1975.

This invention relates to a method of cultivating tobacco plant thereby increasing the yield of tobacco leaves, characterized in that after topping of tobacco plant during cultivation, the tobacco leaves are sprayed with an aqueous solution of choline salt of maleic hydrazide, thereby preventing the growth of suckers and, at the same time, increasing the yield of tobacco leaves.

More particularly, the invention is concerned with a method of cultivating tobacco plant thereby increasing the yield of tobacco leaves, characterized in that after topping of tobacco plant during cultivation, the tobacco leaves are sprayed with an aqueous solution containing 1,000 to 8,000 p.p.m. of choline salt of maleic hydrazide.

In the cultivation of tobacco plant, it has heretofore been an ordinary practice, for the increase in yield of desired leaves and for the enhancement in quality of tobacco leaves, that tip-buds of tobacco plant are removed (referred to as "topping") on about the 60th to 70th day after transplantation of tobacco. When tobacco plant is subjected to topping, however, suckers grow to greatly disturb the growth of normal leaves, with the result that the tobacco leaves are not only decreased in yield but also degraded in quality. Several days later, therefore, it is necessary to remove the suckers. At this stage, however, the stalks and leaves of tobacco plant have grown to a great extent, so that it is quite troublesome to carry out the sucker-removing operation which requires a great deal of labor. In order to save the labor required for the sucker-removing operation, various methods of preventing the development of suckers by use of chemicals have come to be studied in recent years, and there has been widely adopted a method of inhibiting the growth of suckers by spraying tobacco leaves, after topping, with an aqueous solution of diethanolamine, potassium or sodium salt of maleic hydrazide. However, the diethanolamine, potassium or sodium salt of maleic hydrazide has such property as to strongly inhibit the growth of substantially all of higher plants, and hence greatly disturbs the growth of normal leaves of tobacco, though the said salt displays a sufficient effect for the prevention of sucker development. Accordingly, the upper leaves under growth, which are particularly susceptible, are extremely inhibited in growth and become smaller in leaf area to be substantially deprived of their value as tobacco leaves. Thus, the above-mentioned method is usually lower in yield and quality of tobacco leaves than the conventional method in which the suckers are removed by manual operation.

With an aim to establish a method of increasing the yield of tobacco leaves without disturbing the growth of tobacco leaves and without allowing the development of suckers, we made extensive studies to accomplish the present invention.

In accordance with the present invention, there is provided a method of cultivating tobacco plant thereby increasing the yield of tobacco leaves, characterized in that tobacco leaves, after topping, are sprayed with an aqueous solution containing 1,000 to 8,000 p.p.m. of a choline salt of maleic hydrazide.

The choline salt of maleic hydrazide used in the present invention is equivalent in sucker growth-inhibiting activity to, or stronger in said activity than, the diethanolamine, potassium and sodium salts of maleic hydrazide which have widely been used hitherto. Surprisingly, however, the upper leaves of tobacco plant, which have been subjected to the present method, grow larger to increase the yield of tobacco leaves to a great extent. This phenomenon is entirely contrary to the fact that the growth of upper leaves is inhibited when the conventional diethanolamine or the like salt of maleic hydrazide is used. The reason for such difference has not been elucidated yet, and is dependent upon the future studies. However, the choline itself is a substance which is universally present in animals and plants of the natural world, and it is considered that the choline might play a certain physiological role in the growth of plants.

The choline salt of maleic hydrazide used in the present invention can be obtained by, for example, reacting triethylamine with ethylene oxide to synthesize choline, and then dissolving maleic hydrazide in the choline.

A preferred embodiment of the present method is such that the whole surfaces of stalks and leaves of tobacco plant after topping are sufficiently sprayed 1 to 2 times with 100 to 150 liters per 10 acres (=¼ acres) of an aqueous solution containing 1,000 to 8,000 p.p.m., preferably 3,000 to 5,000 p.p.m., of choline salt of maleic hydrazide. In general, the aqueous solution of the choline salt of maleic hydrazide is preferably used in admixture with a commercially available nonionic or anionic surfactant in order to impart thereto adhesiveness onto and penetrability into the stalks and leaves of tobacco.

The effects of the present invention are illustrated below with reference to an example. Although such example will be given in detail with reference to the specific tobacco plant and other specific conditions, it should be understood that the present invention is applicable to all the variety of tobacco plants including burley, dark fire, Maryland and cigar tobaccos, and that those skilled in the art can make any modification of the present invention without departure from its spirit and scope.

The drawings are graphs showing the results of the example, in which

FIG. 1 shows the area of tobacco leaves, and

FIG. 2 shows the weight of tobacco leaves.

In each drawing, the curves 1, 2, 3 and 4 show the cases where there were used, respectively, the choline, potassium, sodium and diethanolamine salts of maleic hydrazide.

EXAMPLE

Tobacco plants of the species Bright Yellow were grown in unglazed pots. On April 20, the tobacco plants were sprayed with an aqueous solution of each of sodium, potassium, diethanolamine and choline salts of maleic acid hydrazide, and on May 25, i.e. after 35 days from the spraying, the tobacco leaves were measured in area and weight.

The sucker-controlling effects of each salt of maleic hydrazide at various concentrations were as shown in Table 1. The sucker-controlling effects were represented by numerical values of 5 grades, where 5 shows that the effects was markedly excellent, 1 shows that the effect was scarce, and 2 to 4 show intermediary effects in order of 2, 3 and 4 between the said two effects.

Table 1

| Concentration | Sucker-controlling effects | | | |
| --- | --- | --- | --- | --- |
| | Sodium salt | Potassium salt | Diethanolamine salt | Choline salt |
| 3,000 p.p.m. | 5 | 5 | 5 | 5 |
| 1,000 p.p.m. | 3 | 2 | 4 | 3 |
| 500 p.p.m. | 2 | 1 | 2 | 2 |

The area and weight of tobacco leaves, when each salt was used at a concentration of 3,000 p.p.m., were as shown in FIGS. 1 and 2.

As is clear from the above test results, the sucker-controlling effects of the salts of maleic hydrazide were in order of amine salt > choline salt > sodium salt > potassium salt. Further, among the salts used at a concentration of 3,000 p.p.m., the choline salt was particularly excellent in effectiveness on the area and weight of tobacco leaves, as shown in FIGS. 1 and 2.

What we claim is:

1. A method of cultivating tobacco plants thereby increasing the yield of tobacco during cultivation, which comprises spraying the tobacco leaves with an aqueous solution containing 1,000 to 8,000 p.p.m. of a choline salt of maleic hydrazide.

2. A method as claimed in claim 1, wherein the choline salt concentration of said aqueous solution is 1,000 to 5,000 p.p.m.

* * * * *